| United States Patent [19] | [11] Patent Number: 4,780,414 |
| Nimrod et al. | [45] Date of Patent: Oct. 25, 1988 |

[54] METHOD OF PRODUCING HIGH MOLECULAR WEIGHT SODIUM HYALLRONATE BY FERMENTATION OF STREPTOCOCCUS

[75] Inventors: Abraham Nimrod; Benjamin Greenman; Dov Kanner, all of Rehovot; Moshe Landsberg, Petah Tikva; Yaffa Beck, Gedera, all of Israel

[73] Assignee: Bio-Technology General Corp., New York, N.Y.

[21] Appl. No.: 815,957

[22] Filed: Jan. 9, 1986

Related U.S. Application Data

[63] Continuation-in-part of Ser. No. 692,692, Jan. 18, 1985.
[51] Int. Cl.$^4$ .................. C12P 19/04; C12N 1/20; C12R 1/46
[52] U.S. Cl. .................. 435/101; 435/253; 435/803; 435/818; 435/885
[58] Field of Search .............. 435/701, 253, 801, 803, 435/818, 885; 536/55.1, 123; 514/54, 62, 847, 915

[56] References Cited

U.S. PATENT DOCUMENTS 4,517,295 5/1985 Bracke et al. .................. 435/885

FOREIGN PATENT DOCUMENTS 0037001 3/1983 Japan .................. 536/55.1

OTHER PUBLICATIONS

Buchanan et al.; 'Recovery of Microorganisms from Synovial and Pleural Fluids of Animals Using Hyperosmolar Media'; *Veterinary Microbiology,* vol. 7 (1982); pp. 19–33.

Woolcock, J. B.; 'The Capsule of *Streptococcus equi*', *J. of Gen. Microbial,* vol. 85 (1974); pp. 372–375.

Holmstrom B. et al.; 'Production of Hyaluronic Acid by a Streptococcal Strain in Batch Culture'; *Appl. Microbial.,* vol. 15, No. 6, (1967) pp. 1409–1413.

*Primary Examiner*—Elizabeth Weimar
*Attorney, Agent, or Firm*—John P. White

[57] ABSTRACT

A novel mutant microorganism *Streptococcus zooepidemicus* HA-116 ATCC 39920, has been produced. The microorganism produces large amounts of high molecular weight hyaluronic acid. The invention provides a method of obtaining such microorganisms.

The invention also concerns a method of obtaining sodium hyaluronate which comprises growing with vigorous agitation a microorganism of the genus Streptococcus under appropriate conditions in a suitable nutrient medium containing a sugar component as a carbon source. The sugar component is present in a substantially constant concentration between 0.2 and 10 grams per liter. The medium has a substantially constant pH between about 6.0 and 7.5 and includes a substantially constant magnesium ion concentration above 0.05 grams per liter. The sodium hyaluronate excreted into the medium by the organism is purified using methods involving precipation, redissolving and reprecipating the hyaluronate. Composition of sodium hyaluronate which are characterized by an absence of pyrogenicity and skin irritation are obtained.

38 Claims, No Drawings

METHOD OF PRODUCING HIGH MOLECULAR WEIGHT SODIUM HYALLRONATE BY FERMENTATION OF STREPTOCOCCUS

This application is a continuation-in-part of U.S. Ser. No. 692,692, filed Jan. 18, 1985, the contents of which are hereby incorporated by reference into the present application.

BACKGROUND OF THE INVENTION

This invention concerns a process for the production of the sodium salt of high molecular weight hyaluronic acid by large-scale fermentation of a microorganism of the genus Streptococcus.

Hyaluronic acid is a naturally occurring glycosaminoglycan consisting of a linear polymer of molecular weight of 50,000-13,000,000 daltons. It is a polysaccharide made of a repeating units of glucuronic acid and N-acetyl-glucosamine, bound by alternating 1-3 and 1-4 bonds.

Hyaluronic acid is present in various connective tissues of animals, such as skin and cartilage. Some organs are specifically rich in hyaluronic acid, such as the umbilical cord, synovial fluid, the vitreous humor and rooster combs. In addition, hyaluronic acid is produced by various microorganisms, such as streptococci Type A and C.

In skin and cartilage, the role of hyaluronic acid is to bind water and retain the tonicity and elasticity of the tissue. In joint fluids, the viscous hyaluronic acid solution serves as a lubricant to provide a protective environment to the cells. A solution of ultrapure hyaluronic acid from rooster combs has been in use for several years as a supportive medium in opthalmic surgery, see U.S. Pat. No. 4,141,973 of E. A. Balazs (1979). A similar preparation has been shown to be beneficial in the treatment of inflamed knee joints of race horses. Another use of hyaluronic acid results from its highly hydrophilic nature, making it an ideal constituent of moisturization lotions for cosmetic use, U.S. Pat. No. 4,303,676 of E. Balazs (1981).

Hyaluronic acid has been isolated from the various biological sources, as described above, including microbial broth. The isolation and characterization of hyaluronic acid has been described by Meyer et al., J. Biol. Chem. 107,629 (1934); J. Biol. Chem. 114,689 (1936), and has recently been reviewed in Methods in Enxymol. 28, 73 (1972). The structure of hyaluronic acid was elucidated by Weissman et al., J. Am. Chem. Soc. 76, 1753 (1954) and Meyer, Fed. Proc. 17, 1075 (1958).

The production of hyaluronic acid by Streptococcus was first shown by Forrest et al., J. Biol. Chem. 118, 61 (1937), and further elaborated on since by various researchers, such as Roseman et al., J. Biol. Chem 203,213 (1953), Pierce and White, Proc. Soc. Exp. Biol. Med. 87, 50 (1954), U.S. Pat. No. 2,975,104 of G. H. Warren (1961), and Sunghara et al., J. Biol. Chem. 254, 6252 (1979), demonstrating the identity of hyaluronic acid from animal and microbial sources. Procedures have been published for batch fermentations of Type A streptococci and hyaluronic acid isolation on small to medium scales Thonard et al., J. Biol. Chem. 239, 726 (1964); Holmstrom and Ricica, Appl. Microbio. 15, 1409 (1967); Kjems and Lebech, Acta Path. Microbiol. Scand. 84, 162 (1976). These procedures included anaerobic fermentations of the pathogenic bacteria, and resulted in yields of 0.4-1 grams/liter of hyaluronic acid of a molecular weight of 700,000 or less.

Other procedures have concerned the aerobic fermentation of streptococci to produce hyaluronic acid such as Japanese Patent Publication Kokai No. 58-056692, published April 4, 1983, by inventors, Akasaka H, et al. Other publications such as, U.S. Pat. No. 4,141,973, Feb. 27, 1979 by E.A. Balazs, concerned the production and purification of hyaluronic acid from sources such as animal connective tissue. The hyaluronic acid production and purification procedures disclosed in the prior art did not, however, yield hyaluronic acid of an average molecular weight of greater than $2.0 \times 10^6$ daltons. This is largely due to the fact that hyaluronic acid is easily degraded by shearing or oxidized in reactions catalyzed by impurities or metal ions present in the hyaluronic acid composition.

The novel process described herein results in hyaluronic acid of a molecular weight from about $1 \times 10^6$ to about $4.0 \times 10^6$ daltons, in a yield of about 2 grams/liter in anaerobic fermentation and about 4-6 grams/liter in aerobic fermentation. This was made possible by producing a mutant strain of a Type C *Streptococcus zooepidemicus*, HA-116, ATCC 39920, which is a high producer of hyaluronic acid and is haemolysin minue, i.e. of negligible pathogenicity. Aerobic Fermentation of *S. zooepidemicus*, HA-116, ATCC 39920 and subsequent purification of hyaluronate have resulted in batches of sodium hyaluronate with an average molecular weight of greater than $3.5 \times 10^6$ daltons. This invention is the first method of producing and purifying such high molecular weight sodium hyaluronate by bacterial fermentation.

Hyaluronic acid that is non-pyrogenic and non-irritating can be obtained employing the methods of this invention. Other methods also within the scope of this invention can be employed to produce ultra-pure, non-inflammatory hyaluronic acid suitable for clinical use.

SUMMARY OF THE INVENTION

The invention concerns a microorganism of the species *Streptococcus zooepidemicus*, HA-116, ATCC 39920, and mutants derived therefrom which are capable of producing sodium hyaluronate by fermentation and excreting it into the surrounding medium.

The invention also concerns a method of obtaining sodium hyaluronate which comprises growing with vigorous agitation a microorganism of the genus Streptococcus under appropriate conditions in a suitable nutrient medium. The medium includes a sugar component as the carbon source in a substantially constant concentration between about 0.2 and 10 grams per liter, has a substantially constant pH between about 6.5 and 7.5 and also includes a substantially constant magnesium ion concentration above 0.05 gram per liter. The microorganism produces sodium hyaluronate and excrete it into the medium. The sodium hyaluronate is then recovered from the medium.

The sodium hyaluronate is recovered from the medium by a method comprising treating in the medium containing the microorganism so as to remove the microorganism and other materials insoluble in the medium, precipitating the sodium hyaluronate from the medium, e.g. precipitation with organic solvents, and recovering the precipitate. The precipitate can then be ground and dried. Compositions of sodium hyaluronate characterized by an absence of pyrogenicity and inflammatory activity can be produced by these methods.

The present invention also concerns a method for selecting microorganisms which produce enhanced amounts of hyaluronic acid and which lack hemolytic activity. The method comprises treating microorganisms that produce hyaluronic acid with a suitable mutagen to produce mutants thereof, and growing the mutants on a suitable solid medium. The mucoid colonies are identified, and recovered. The recovered colonies are grown on blood agar and colonies which do not lyse hemoglobin are selected.

DETAILED DESCRIPTION OF THE INVENTION

The present invention concerns a method of obtaining high molecular weight sodium hyaluronate from microorganisms of the genus Streptococcus, e.g. S. zooepidemicus or S. equisimilis. The method comprises growing microorganisms of the genus Streptococcus with vigorous agitation under appropriate conditions and in a suitable nutrient medium. The medium includes a sugar component as the carbon source in a substantially constant concentration between about 0.2 and 10 grams per liter, a substantially constant magnesium ion concentration above about 0.05 grams per liter and a substantially constant pH between about 6.5 and 7.5. The microorganisms produce sodium hyaluronate and excrete it into the medium. The sodium hyaluronate is then recovered from the medium.

Any hyaluronic acid producing species of Streptococcus can be used in practicing this invention, e.g. S. zooepidemicus, S. equisimilis or S. pyogenes. The preferred species is S. zooepidemicus and the strain is S. zooepidemicus HA-116 ATCC 39920 which is a mutant strain produced according to a method of this invention for obtaining microorganisms which produce an enhanced amount of hyaluronic acid.

The sodium hyaluronate can be obtained by growing the Streptococcus under aerobic or anaerobic conditions. In a preferred embodiment of the invention the appropriate growing conditions comprise aeration of the medium at a rate greater than about 0.5 volumes of air per volume of medium per minute (vvm). An aeration rate of 1–2 vmm is generally used, however greater aeration rates may be desirable. In this preferred embodiment the suitable nutrient medium comprises per liter, casein hydrolysate about 10 to 30 grams, yeast extract about 5 to 15 grams, NaCl about 2 grams, $MgSO_4.7H_2O$ above about 0.5 grams, $K_2 HPO_4$ about 2.5 grams, and glucose about 2 to 15 grams.

The sodium hyaluronate can be recovered by treating the medium containing the microorganism so as to remove the microorganism and other materials insoluble in the medium, e.g. by filtration or centrifugation. The sodium hyaluronate is then precipitated from the medium and recovered. The precipitate can then be ground to uniform size particles and dried.

In one embodiment of the invention the sodium hyaluronate is recovered by adjusting the pH of the medium containing the microorganism to a pH of about 5.0 and then heating the medium for a suitable period of time at a temperature between about 80° and 95° C., e.g. heating for 20 minutes at a temperature of about 90° C. or preferably heating for 40 minutes at 80° C. After heating the microorganisms and other insoluble materials are removed. The preferred method of removal is by filtration with a filter aid such as diatomaceous earth.

The sodium hyaluronate can be precipitated from the medium or filtrate by adding a first organic solvent, such as isopropanol, to the medium. The precipitate is redissolved in 3% aqueous sodium acetate and then reprecipitated with a second organic solvent such as ethanol. The second precipitate is redissolved in 3% aqueous sodium acetate and activated charcoal is added to form a suspension. The suspension is filtered and a third organic solvent e.g. acetone is added to produce a precipitate of sodium hyaluronate. The first, second and third organic solvent can each be isopropanol, ethanol or acetone. Alternatively the hyaluronate can be precipated by the same organic solvent in each step, e.g. sodium hyaluronate is precipitated from the medium by using isopropanol in all three of the precipitation steps.

In another embodiment of the invention the pH of the medium containing the microorganism is adjusted to about 7.0 and the medium is cooled to a temperature between about 4° C. and 15° C. and preferably between about 4° and 20° C., prior to treating the medium to remove the microorganism. The medium is then diluted with 3% aqueous sodium acetate to the extent necessary to permit subsequent treatment e.g. three to four-fold.

In one embodiment of the invention, the sodium hyaluronate precipitate is redissolved in 0.15M aqueous NaCl and cetyl-pyridinium chloride is added to form the cetyl-pyridinium salt of hyaluronic acid. The cetyl-pyridinium salt is dissolved in aqueous NaCl and 15% ethanol, e.g. at least 1M NaCl and sodium hyaluronate is recovered therefrom by addition of organic solvent e.g. ethanol precipitating the sodium hyaluronate.

This sodium hyaluronate precipitate can be redissolved in 0.15M aqueous NaCl. Cetyl-pyridinium chloride is added to again form the cetyl-pyridinum salt of hyaluronic acid. The hyaluronic acid salt is dissolved in NaCl (at least about 1M) and ethanol and the sodium hyaluronate is recovered by addition of organic solvent. The precipitate is thereafter dissolved in sterile aqueous 1M NaCl and the resulting solution is contacted with a magnesium silicate absorbant, e.g. Florisil, to remove impurities and residual cetyl-pyridinium ions. The solution is then sterilized and sodium hyaluronate is precipitated by the addition of sterile organic solvent, e.g. sterile isopropanol. The sodium hyaluronate so produced can be air dried under sterile conditions.

In another embodiment of the invention, the medium after fermentation and heating but before microorganisms removal is treated with a first organic solvent. The sodium hyaluronate thus precipitated is recovered, redissolved in 3% aqueous sodium acetate and then activated charcoal is added to form a suspension. The suspension is filtered with a filter aid such as diatomaceous earth and an organic solvent is added to produce a precipitate of sodium hyaluronate. This precipitate is then ground and dried.

In another embodiment of the invention the pH of the medium containing the microorganism is adjusted to about 7.0 and the medium is cooled to a temperature between about 4° and 20° C. prior to treating the medium.

In a preferred embodiment of the invention, an organic solvent, such as ehtanol, is added to the medium containing the microorganisms and the precipitate is collected and washed thoroughly with the organic solvent. The sodium hyaluronate precipitate is redissolved in 0.15M aqueous NaCl and activated charcoal is added. The resulting suspension is filtered with a diatomaceous earth filter aid to remove the charcoal, microorganisms and other insoluble materials. The clear filtrate is then treated with cetyl-pyridinium chloride to form the insoluble cetyl-pyridinium salt of hyaluronic acid. The cetyl-pyridinium salt is collected and dissolved in aqueous NaCl containing 10% (v/v) ethanol, e.g. at least 1M NaCl, and sodium hyaluronate is recovered therefrom by addition of organic solvent, e.g. ethanol.

This sodium hyaluronate precipitate can be redissolved in 0.15M aqueous NaCl. Cetyl-pyridinium chloride is added to again form the cetyl-pyridinium salt of hyaluronic acid. The hyaluronic acid salt is dissolved in NaCl (at least about 1M) with 10% ethanol and the dosium hyaluronate is recovered by addition of organic solvent. The precipitate is thereafter dissolved in sterile aqueous 1M NaCl and the resulting solution is contacted with a magnesium silicate absorbant, e.g. Florisil to remove impurities and residual cetyl-pyridinium ions. The solution is then sterilized by filtration and sodium hyaluronate is precipitated by the addition of sterile organic solvent, e.g. sterile ethanol. The sodium hyaluronate so produced can be air dried under sterile conditions.

The sodium hyaluronate is suitable for use in compositions of cosmetic grade and clinical grade sodium hyaluronate and other suitable carriers, e.g. glycerol, polypropylene glycol, sorbitol, collagen, polyethylene glycol.

The cosmetic grade composition of sodium hyaluronate produced by the methods of this invention is characterized by an absence of skin irritation. It contains between about 87% and 91% sodium hyaluronate of a molecular weight between about 700,000 and 1,500,000 daltons and a ratio of glucoronic acid to N-acetyl glucosamine of 1:1, from about 8% to about 12% by weight water, from about 4% to about 5% by weight sodium ion, less than about 0.1% by weight protein, less than about 0.05% by weight sulfate, and less than about 0.5% by weight nucleic acid.

The clinical grade composition of sodium hyaluronate of this invention is characterized by an absence of pyrogenicity and inflammatory activity. It contains between about 88% and 92% by weight sodium hyaluronate of an average molecular weight from about 2 to about $3.5 \times 10^6$ daltons and a glucuronic acid to N-acetyl glucosamine ratio of 1:1, from about 8% to about 12% by weight water, from about 4% to about 6% by weight sodium ion, less that 0.01% by weight protein, less than 0.001% by weight sulfate, less than 0.02% by weight nucleic acid and less than 0.2% by weight neutral sugar.

A preferred ultrapure composition of sodium hyaluronate produced by the methods of this ivention is characerized by a minimum limiting viscosity of about 3.5m3/kg, a minimum average molecular weight of about $3.5 \times 10^6$ daltons, a specific optical rotation measured at 25° C. and at a wavelength of 436nm from about 155° to 165°, a protein content of less than about 1mg/gram, an absorbance at the wavelength of 257nm of less than about 0.5, endotoxin of less than about 0.05ng/ml., less than about 0.2mg/g of iron, less than about 0.2mg/g of copper, and an infiltration of less than about 200 white blood cells per mm$^3$ of aqueous humor of owl monkey eye when 1 ml of a 1% solution of the composition dissolved in physiological buffer is implanted in the vitreous replacing about one-half the existing liquid vitreous.

Compositions of high molecular weight sodium hyaluronate of a average molecular weight greater than $3.5 \times 10^6$ daltons and of different grades of purity have also been produced by the methods of this invention.

The vitreous test in the Owl Monkey Eye was performed essentially as described in U.S. Pat. No. 4,141,973 of E. A. Balazs (1979).

The invention also concerns the microorganism Streptococcus zooepidemicus HA-116 ATCC No. 39920 or mutants derived therefrom. This microorganism was derived by a method of selecting microorganisms which produce an enhanced amout of hyaluronic acid and which lack hemolytic activity. The method comprises treating microorganisms that produce hyaluronic acid, such as microorganisms of the genus Streptococcus, with a suitable mutagen capable of producing mutants of the organism, e.g. nitrosoguanidine. The mutants are grown on a suitable solid medium, e.g. Todd-Hewit agar, and mucoid colonies are identified. These colonies are recovered from the solid medium and grown on blood agar. The colonies which do not lyse hemoglobin are then selected and used for the production of hyaluronic acid in accordance with the methods of this invention.

EXPERIMENTAL DETAILS

BACTERIA SELECTION AND MUTATION

Nitrosoguanidine Mutagenesis

Bacteria of the genus Streptococcus were treated for 40 min with 100 mg/ml of N-methyl-N'-nitro-N- nitrosoguanidine in Tris-maleic buffer, pH 6.0, and then allowed to segregate on Todd-Hewitt agar plates for selection of high producers or on blood agar plates for Hemolysin minus selection. The survival rate of the bacteria was usually about 0.1%. Various Type C *Streptococci* obtained from hospital collections were treated as described above.

Selection for High Production

Visual evaluation of the clones was used for selection of large mucoid colonies. One such colony was obtained from an isolate of a strain which has been typed by the National Streptococcal Reference Center, of the Israeli Ministry of Health, as a variant of Type C *Streptococcus equisimilis* (designated as HA-100). Subsequent tests based on "API 20 Strep" tests (API SYSTEM, S.A. FRANCE) for identification of Streptococci strains, indicate that HA-100 is more closely realted to *S. zooepidemicus.*

Selection for Hemolysin Minus Mutants

Strain HA-100 was subjected to the mutagenis procedure described above and hemolysin minus [hem.(−)] cololies were examined both for hemolysin activity and for hyaluronic acid production in test-tube fermentation. One hem.(−) mutant which was also a high producer of hyaluronic acid was chosen and used for large scale hyaluronic acid production. This mutant was designated HA-116. "API 20 Strep." tests indicate that HA-116 is a strain of *S. zooepidemicus. Streptococcus zooepidemicus* HA-116 has been deposited with the American Type Culture Collection, 12301 Parklawn Drive, Rockville, MD 20852, pursuant to the provisions of the Budapest Treaty on the International Recognition of the Deposit of Microorganisms for the Purpose of Patent Procedure, and has been assigned accession number ATCC 39920.

THE FERMENTATION PROCESS

In addition to the use of the selected mutant HA-116, we have devised several other unique procedures to increase the yields and the molecular weight of the hyaluronic acid produced by bacterial fermentation and to shorten fermentation time. This includes (i) maintenance of high levels of magnesium ion concentrations; and (ii) performance of aerobic fermentations with a high rate of aeration and vigorous agitation.

In a preferred embodiment of the invention the composition of the fermentation medium is as follows:

| Component | Concentration (grams/liter) |
| --- | --- |
| Casein hydrolysate | 20 |
| Yeast extract | 10 |
| NaCl | 2 |
| MgSO$_4$.7H$_2$O | 1.5 |
| K$_2$HPO$_4$ | 2.5 |
| Glucose | 5 |

In a more preferred embodiment of the invention, the concentration in the fermentation medium of MgSo$_4$.7H$_2$O is 1.0g/1, the concentration of glucose is 10g/1 and the other components have the same concentrations as above.

The pH of the medium is maintained at about 7.0 by continuous addition of 5N NaOH upon demand of a pH controller. Concomitant addition of an identical volume of 50% (w/v) glucose is preformed by a pump connected in parallel to the controller.

The cultivation of the bacteria can be conducted with or without aeration. In both cases the cultivation is preferably conducted with vigorous agitation. The aeration is preferably at a rate of about 1–2 volume of air per volume of medium per minute. Yields in the non-aerated fermentors are from about 2 to about 3 g/1 of hyaluronic acid with an average M.W from about 1.5 to about $2 \times 10^6$. Fermentation with aeration yields from about 4 to about 6 g/1 of hyaluronic acid with an average M.W of from about 2.2 to about $3.3 \times 10^6$. The average M.W is determined based on viscosity measurements known to those of ordinary skill in the art. In both cases, the incubation time is around 12 hours when a 5% (v/v) incoculum of bacteria which has been grown to 2.0–2.5 O.D. units measured at 660 nm is used. At the end of the fermentation, the density of the biomass is equivalent to a turbidity of 8–13 O.D. units.

ISOLATION AND PURIFICATION OF HYALURONIC ACID

The hyaluronic acid may be purified by three different procedures, Procedure I, II and III.

PURIFICATION PROCEDURE I

Purification Procedure I can be divided into two stages A and B. Stage A yields a "cosmetic grade" sodium hyaluronate, while Stage B which is a further purification of the cosmetic grade obtained in Stage A yields a high purity, non-inflammatory material suitable for clinical application.

Stage A

This stage comprises the removal of the bacteria and other insoluble materials by filtration, followed by three successive sedimentation by isopropanol and treatment with activated charcoal.

When only cosmetic grade material is prepared, the fermentation broth is heated for 20 minutes at a temperature of about 90° C. and at a pH of about 5.0 prior to filtration. At this time no dilution is necessary. For the preparation of a clinical-grade high molecular weight material, the fermentation broth is cooled with ice to a temperature from about 10° to about 15° C., diluted 3- to 4-fold with 3% sodium acetate, adjusted to a pH of about 7.0 and then subjected to filtration. Diatomaceous-earth type filter-aid, e.g. .5 grams/liter of Celatom FW-14, Eagle-Picker Industries, Inc., Cincinnati, OH, is used in conjunction with a vacuum-type or pressure filter. Sodium hyaluronate is precipitated from the filtrate by addition of 1 volume of isopropanol. The precipitate is redissolved in an equal volume of 3% sodium acetate, and the material precipitated again with isopropanol. The second precipitate is redissolved in 3% sodium acetate, then 1 gram/liter of activated charcoal is added and the mixture is stirred for about 1 hour. This suspension is filtered and the sodium hyaluronate is precipitated by addition of isopropanol, washed with isopropanol and finally ground and air-dried to give a "cosmetic-grade" product.

Stage B

Cosmetic-grade sodium hyaluronate is purified by two successive precipitations of its cetyl-pyridinium salt, followed by adsorption of impurities on a magnesium silicate, e.g., FLORISIL ®, columnn. FLORISIL ® is a registered trademark of Floridin Co., Berkley Springs, W.Va.

Cetyl-Pyridinium Chloride (CPC) Precipitation:

Cosmetic grade material from Stage A is dissolved in 0.15M NaCl to give a hyaluronate solution of a concentration of about 0.25 percent. One volume of 10% CPC is 0.15M NaCl is added to about 8 volumes of the 0.25% hyaluronate solution. The cetyl-pyridinium salt is separated by decantation and centrifugation, washed with 0.15M NaCl and then redissolved in 2M NaCl containing 15% ehtanol, to give a solution of about 0.2% hyaluronate. Hyaluronic acid is sedimented as the sodium salt by addition of 1 volume of isopropanol. The pellet is washed with isopropanol and redissolved in 0.15M NaCl as described above and the CPC precipitation process is repeated. The isopropanolic precipitate obtained from the second CPC precipitation is then redissolved in 1M NaCl for FLORISIL ® treatment.

Florisil Adsorption:

A solution of about 0.25% sodium hyaluronate in pyrogen-free 1M NaCl is passed through a column of 30–60 mesh activated FLORISIL ® e.g. 200 gr Florisil per 10 liter of solution. The solution is then rendered germ-free by filtration through a 0.2 m filter. Sodium hyaluronate is precipitated by filter-sterilized isopropanol (1 volume), followed by washing with sterile analytical grade ethanol. The precipitate is finally dried by a stream of sterile air.

The yield of hyaluronic acid in this procedure is about 60–70%.

PURIFICATION PROCEDURES II AND III

Alternatively, two independet purification methods may be employed to obtain cosmetic grade and clinical grade sodium hyaluronate. These procedures are preferred procedure for obtaining sodium hyaluronate. Procedure II yields a low molecular weight "cosmetic grade" sodium hyaluronate, and Procedure III yields a high purity, high molecular weight non-inflammatory sodium hyaluronate suitable for clinical application.

Procedure II

At the conclusion of fermentation, the fermentation broth is heated to about 90° C., then the pH is adjusted to about 5.0 and the medium kept at 80° for 40 minutes.

This step is terminated by adjusting the pH to 7.0 and cooling to about 20° C. This heating process brings about a drop in the molecular weight of the hyaluronate to about $1-1.5 \times 10^6$ dalton.

The sodium hyaluronate is precipitated from the fermentation mixture by addition of 1.5 volumes of ethanol. The precipitate is further washed with ethanol to eliminate a larger portion of the microorganisms. This crude material is redissolved in aqueous 3% sodium acetate containing 0.1% parahydroxybenzoic acid methyl ester. The volume is adjusted to give about 2-3 grams per liter of hyaluronate. One gram per liter of activated charcoal and 40 grams per liter of a distomaeous earth-type filter-aid, e.g. Celatom FW-14, Eagle-Picker Industries, Inc., Cincinnati, Ohio, are added to the solution and stirred for at least 1 hour. The mixture is then filtered through a filter-aid cake. Sodium hyaluronate is precipitated by addition of 1.5 volumes of ethanol and the precipitate is redissolved in an equal volume of 3% sodium acetate. This solution is filtered through a fine-pore cotton cartridge and then treated with 1.5 volumes of ethanol. The precipitated purified sodium hyaluronate is ground and finally air-dried to give a "cosmetic grade" product.

Procedure III

In this procedure, the fermentation broth is treated with 1.5 volumes of ethanol immediately following the conclusion of the fermentation. The precipitated sodium hyaluronate is washed with ethanol to get rid of a large portion of the microorganisms and then redissolved in aqueous 0.15M NaCl containing 0.1% parahydroxybenzoic acid methyl ester. The volume is adjusted to give 1-2 grams per liter of hyaluronate. One gram per liter of activated charcoal and 40 grams per liter of Celatom FW-14 are added to the solution and the mixture stirred for 1 hour. The suspension is then filtered through a cake of filter-aid.

Cetyl-Pyridinium Chloride (CPC) Precipitation

A 10% solution of CPC in 0.15M NaCl is added to the clear hyaluronate solution. The amount of added CPC solution is calculated to give 5 times in weight the amount of hyaluronic acid. The precipitated cetyl-pyridinium salt is separated by decantation and centrifugation, then redissolved in 1M NaCl containing 10% ethanol by volume to give a solution of about 1-2 grams per liter. Sodium hyaluronate is precipitated by addition of 1.5 volumes of ethanol.

After redissolving the precipitate in 0.15M NaCl the CPC precipitation process described in the immediately preceding paragraph is repeated. The ethanolic precipitate obtained after the second CPC process is then taken for the final purification step.

FLORISIL ® Adsorption

A solution of about 0.1-0.15% sodium hyaluronate in sterile pyrogen-free 1M NaCl is passed through a column of 30-60 mesh activated FLORISIL ® e.g. 20 gr Florisil per liter of solution. The solution is then rendered germ-free by filtration through a 0.2 um filter. Sodium hyaluronate is precipitated by ethanol (1.5 volumes), followed by washing with analytical grade ethanol. The precipitate is finally dried by a stream of sterile nitrogen.

The yield of hyaluronic acid in this procedure is about 70-80%.

PROPERTIES OF THE PRODUCT SODIUM HYALURONATE

Sodium Hyaluronate Grade I

Sodium hyaluronate grade I is "cosmetic grade" sodium hyaluronate that is obtained after purification Stage A of Procedure I or Procedure II. Its properties are as described below:

a. Content of Sodium Hyaluronate:

87-91%, assayed by the modified carbazole method, Bitter and Muir, Anal. Biochem. 4, 330 (1962) using Sigma hyaluronic acid Type I, cat. #H 1751, as a reference standard.

b. Average Molecular Weight:

From about 700,000 to about 1,500,000 daltons, calculated from the limiting viscosity number esentially as described by Laurent et al., Biochem. Biophys. Acta 42, 476 (1960). A representative calculation of intrinsic viscosity of molecular weight is shown below.

Intrinsic Viscosity of Molecular Weight:

The viscosity of sodium hyaluronate (NaHA) solutions was measured with a capillary viscometer. The flow time (t) of the sample was measured and compared with the flow time (t) of pure solvent.

Viscometer: Cannon-Ubbelohde dilution viscometer size 100 (Cannon Instrument Co.).

Solution: 0.1% sodium hyaluronate in 0.2 M sodium chloride

Temperature: 25° C. +0.01

Calculation of instrinsic viscosity:

$\eta$rel. - Relative viscosity expresses the change in solution viscosity relative to the pure solvent.

$$\eta\text{rel.} - \frac{\eta \text{sample}}{\eta \text{reference}} = \frac{\rho \text{sample} \times t \text{ sample}}{\rho \text{reference} \times t \text{ reference}}$$

$\rho$ - density $t$ - flow time in seconds $\eta sp$ - Specific viscosity. Measures the increase in viscosity over unity.

$$\eta sp - \frac{t \text{ sample} \times t \text{ reference}}{t \text{ reference}} = ref - 1$$

$\eta sp/C$ - reduced viscosity $C$ - concentration in $gr/ml$ $(\eta)$ - intrinsic viscosity (limiting viscosity number)

$(\eta) = c\lim_0 \eta^{sp/C}$

Determination of intrinsic viscosity $(\eta)$:

The viscosity of a 0.1% sodium hyaluronate solution and of two fold, three fold and four fold dilutions of this solution were measured. The concentration of sodium hyaluronate was determined by the carbozole method. sp/C was plotted versus C and extrapolated linearly to C=0. $(\eta)$ was obtained from the intersect of the line with the Y-axis.

Determination of molecular weight:

The molecular weight of sodium hyaluronate was calculated from the empirically-established Mark-Houwink relationship $$(\eta) = 0.0403 \cdot M^{0.775}$$

wherein M is the molecular weight in daltons. The above relationship was used to determine the molecular weight of various lots of NaHA produced. The relationship is shown in Table I.

TABLE I

| $[\eta]$, ml/g | Mol. Wt., Dalton |
| --- | --- |
| 800 | 350,000 |
| 1,200 | 590,000 |
| 1,600 | 860,000 |
| 2,000 | 1,145,000 |
| 2,600 | 1,600,000 |
| 3,200 | 2,100,000 | c. Ratio of Glucuronic Acid/N-Acetyl Glucosamine (NAG): 1/1; NAG assayed by the modified method of Morgan and Elson, methods in Carbohydrate Chemistry 8, 89 (1980).

d. WATER CONTENT: 10%±2%.

e. Protein: Less than 0.1%, assayed by the Coomasie blue method of Bradford, Anal. Biochem. 72, 248 (1976).

f. Sodium Ions: 5%+1%, assayed by flame photometry.

g. Sulfate Content: Less than 0.05%, as determined after hydrolysis in hydrochloric acid by the turbidometric method of Roden et al., Methods Enzymol. 28, 73 (1972).

h. Nucleic Acids: Less than 0.5%, assayed by measurement of the absorbance of light through a 1% solution at a wavelength of 260 m.

i. Absence of Skin Irritation: This is determined for a 1% solution by (i) Draize dermal irritation test in rabbits, Draize, J.H., in: "Appraisal of the Safety of Chemicals in Food, Drugs and Cosmetics". Association of Food and Drug Officials of the United States, Austin, Texas, pp. 46-49 (1959); (ii) Delayed contact hypersensitivity test in Guinea pigs, Magnusson and Kligman, J. Invest. Dermatol. 52, 268 (1969).

Sodium Hyaluronate Grade II

Sodium hyaluronate Grade II is "clinical grade" sodium hyaluronate obtained after purification through Stage B of Procedure I or after purification by Procedure III. Its properties are as described below:

a. Content of Sodium Hyaluronate: 88-92%.

b. Average Molecular Weight: More than $7 \times 10^5$ daltons, usually in the range from about 2 to about $3.5 \times 10^6$ daltons for NaHA purified through Stage B of Procedure I and in the range from about 2 to about $4.4 \times 10^6$ daltons for NaHA purified by Procedure III. These molecular weight ranges are calculated from the limiting viscosity number as described above.

c. Ratio of Glucuronic Acid/N-acetyl Glucosamine: 1/1.

d. Water Content: 10%±2% e. Protein: Undetectable (less than 0.01%).

f. Sodium Ions: 5%±1% g. sulfate Content: Undetectable (less than 0.001%).

h. Nucleic Acids: Undetectable (less than 0.02%).

i. Neutral Sugars: Undetectable (less than 0.2%). The neutral sugars are determined in samples after hydrolysis. Hydrolysis is for 1 hour at 120° C. in 2N trifluoroacetic acid followed by vacuum drying. Thin layer chromatography is preformed on silicagel thin layer plates (0.2 mm), pretreated with 0.02 M sodium acetate. Sample hydrolysates are loaded along with reference standards and run in acetone: water, 90:10. The sugar spots are detected by charring with sulfuric acid.

j. Pyrogenicity: Negative. Pyrogenicity is measured by the standard methods known to those of ordinary skill in the art, after injection of a 1% solution in rabbits.

k. Absence of Inflammatory Activity: This property is determined of a sensitive assay method utilizing mice. The method is based on the migration of white blood cells, mainly polymorphonuclear cells and macrophages, into the peritoneum after introduction of an inflammatory agent. These cells are sensitized by the inflammatory process to produce superoxide radicals. The migration and sensitization are assayed by the following procedure: 1 ml samples are injected intraperitoneally, into groups of 2 to 3 mice. 24 hours later the peritoneum of each animal is washed 3 times with 5 ml of Earle's medium. The washes from the mice in each group are combined. Cells are sedimented at 1,500 RPM for 10 min, and resuspended in 1 ml for counting. The volumes of the samples are then adjusted to give $4 \times 10^6$ cells/ml, and 0.25 ml portions are taken for 90 min incubation with 0.5 ml of 2 mg/ml cytochrome C and graded amounts (0, 2, 10, and 20 mg final) of phorbol myristate acetate (PMA). PMA is an activator of the oxidative "burst" system. The media are centrifuged at 1,500 RPM for 15 min and the absorbance of the supernatants is determined at 550 nm.

Inflammation is indicated by an increase in both the number of peritoneal cells and the maximal ability to respond to PMA and reduce the cytochrome C. Hence, an index of inflammation is defined as the activity (in nmoles of superoxide radicals formed) of all the while cells obtained from one mouse. A sample is regarded as non-inflammatory if the inflammation index is not significantly higher than that obtained from mice injected with saline alone.

What is claimed is:

1. The microorganism Streptococcus zooepidemicus HA-116 ATTC No. 39920 and mutants derived therefrom.

2. A method of obtaining sodium hyaluronate which comprises (a) growing a microorganism of the genus Streptococcus under appropriate conditions in a suitable nutrient medium, the conditions comprising vigorous agitation and aeration of the medium and the medium including a sugar component as the carbon source in a substantially constant concentration between about 0.2 and 10 grams per liter, having a substantially constant pH between about 6.5 and 7.5 and including a substantially constant magnesium ion concentration above about 0.05 grams per liter, such that the microorganism produces sodium hyaluronate and excretes the sodium hyaluronate so produced into the medium, and (b) then recovering the sodium hyaluronate from the medium.

3. A method of claim 2, wherein the microorganism is of the species Streptococcus zooepidemicus.

4. A method of claim 3, wherein the microorganism is Streptococcus zooepidemicus, HA-116, ATCC 39920.

5. The method of claim 2, wherein the aeration of the medium is at a rate greater than about 0.5 volume of air per volume of medium per minute.

6. The method of claim 2, wherein the suitable nutrient medium comprises in the concentration of grams per liter of the medium the following components:

| component | concentration |
| --- | --- |
| Casein hydrolysate | about 10–30 |
| Yeast extract | about 5–15 |
| NaCl | about 2 |
| MgSO$_4$.7H$_2$O | above about 0.5 |
| K$_2$HPO$_4$ | about 2.5 |
| Glucose | about 2–15 |

7. The method of claim 2, wherein recovering the sodium hyaluronate comprises treating the medium containing the microorganisms so as to remove the microorganism and other materials insoluble in the medium, precipitating the sodium hyaluronate from the medium and then recovering the precipitate.

8. The method of claim 7 further comprising grinding and then drying the precipitate.

9. The method of claim 7, further comprising adjusting the pH of the medium containing the microorganism to about 5.0 and then heating the medium for a suitable period of time at a temperature between about 80° and 95° C. prior to treating the medium to remove the microorganism.

10. The method of claim 9, wherein the medium is heated for about 20 minutes at about 90° C.

11. The method of claim 9, wherein the medium is heated for about 40 minutes at about 80° C.

12. The method of claim 7, wherein the treating comprises filtration.

13. The method of claim 12, wherein the filtration comprises filtration on a diatomaceous earth.

14. The method of claim 7, wherein the precipitation comprises adding a first organic solvent to the medium to produce a precipitate, redissolving the precipitate in 3% aqueous sodium acetate, adding a second organic solvent to produce a precipitate, redissolving the precipitate in 3% aqueous sodium acetate, adding activated charcoal to form a suspension, filtering the suspension and adding a third organic solvent to the filtrate to produce a precipitate of sodium hyaluronate.

15. The method of claim 14, wherein each of the first, second and third organic solvents are isopropanol, ethanol or acetone.

16. The method of claim 15, wherein the first, second and third organic solvents are isopropanol.

17. The method of claim 7, further comprising adjusting the pH of the medium containing the microorganism to about 7.0, cooling the medium to a temperature between about 4° and 15° C. and then diluting the medium with 3% aqueous sodium acetate prior to treating the medium to remove the microorganism.

18. The method of claim 7, further comprising adjusting the pH of the medium containing the microorganism to about 7.0, cooling the medium to a temperature between about 4° and 20° C. and then diluting the medium with 3% aqueous sodium acetate prior to treating the medium to remove the microorganism.

19. The method of claim 14, further comprising adjusting the pH of the medium containing the microorganism to about 7.0, cooling the medium to a temperature between about 4° and 15° C. and then diluting the medium with 3% aqueous sodium acetate prior to treating the medium to remove the microorganism.

20. The method of claim 19, further comprising redissolving the precipitate in 0.15M squeous NaCl, adding cetyl-pyridinium chloride to form the cetyl-pyridinium salt of hyaluronic acid, dissolving the cetyl-pyridinium salt in aqueous NaCl (at least about 1M) and ethanol, adding organic solvent and recovering the sodium hyaluronate.

21. The method of claim 20, further comprising redissolving the recovered sodium hyaluronate in 0.15M aqueous NaCl, adding cetyl-pyridinium chloride to again form the cetyl-pyridinium salt of hycluronic acid, dissolving the cetyl-pyridinium salt in aqueous NaCl (at least about 1M) and 10% ethanol, precipitating the sodium hyaluronate with an organic solvent, dissolving the sodium salt in NaCl solution, contacting the resulting solution with magnesium silicate absorbent to remove impurities and residual cetyl-pyridinium ions, sterilizing the solution and adding sterile organic solvent to precipitate the sodium hyaluronate from the solution.

22. The method of claim 21, wherein the organic solvent is isopropanol.

23. The method of claim 21, further comprising airdrying the sodium hyaluronate precipitate under sterile conditions.

24. The method of claim 2, wherein recovering the sodium hyaluronate comprises adding a first organic solvent to the medium to produce a precipitate, washing the precipitate with more organic solvent, redissolving the precipitate in a suitable aqueous solution, adding activated charcoal to form a suspension and filtering the suspension to remove residual microorganisms and other insoluble materials.

25. The method of claim 24, further comprising adjusting the pH of the medium containing the microorganism to about 5.0 and heating the medium for a suitable period of time at a temperature between about 80° and 95° C. prior to adding the first organic solvent.

26. The method of claim 25, wherein the suitable period of time is 40 minutes and the temperature is 80° C.

27. The method of claim 24, wherein the filtration comprises filtration on a diatomaceous earth.

28. The method of claim 24, wherein the suitable aqueous solution 3% sodium acetate.

29. The method of claim 24, further comprising adding a second organic solvent to the filtrate to produce a precipitate, redissolving the precipitate in 3% aqueous sodium actate, filtering the solution and adding a third organic solvent to the filtrate to produce a precipitate of sodium hyaluronate.

30. The method of claim 29, wherein each of the first, second and third organic solvents are isopropanol, ethanol or acetone.

31. The method of claim 29, wherein the first, second and third organic solvents are ethanol.

32. The method of claim 29, further comprising grinding and then drying the precipitate of the third organic solvent.

33. The method of claim 24, 25 or 29, further comprising adjusting the pH of the medium containing the microorganism to about 7.0 and cooling the medium to a temperature between about 4° and 20° C. prior to adding the first organic solvent.

34. The method of claim 24, wherein the suitable aqueous solution is 0.15M aqueous NaCl solution containing 0.1% parahydrozybenzoic acid methyl ester.

35. The method of claim 34, further comprising adding cetyl-pyridinium chloride in 0.15M NaCl to the hyaluronate solution to form the cetyl-pyridinium salt to hyaluronic acid, redissolving the cetyl-pyridinium salt in aqueous NaCl (at least about 1M) containing 10% ethanol and adding organic solvent to recover the sodium hyaluronate.

36. The method of claim 35, further comprising redissolving the recovered sodium hyaluronate in 0.15M aqueous NaCl, adding cetyl-pyridinium chloride to again form the cetyl-pyridinium salt of hyaluronic acid, redissolving the cetyl-pyridinium salt in aqueous NaCl (at least about 1M) containing 10% ethanol, adding organic solvent to precipitate the sodium hyaluronate, redissolving the precipitate in sterile 1M aqueous NaCl, contacting the resulting solution with magnesium silicate absorbent to remove impurities and residual cetyl-pyridinium ions, sterilizing the solution, and adding sterile organic solvent to precipitate the sodium hyaluronate from the solution.

37. The method of claim 36, wherein the organic solvent is ethanol.

38. The method of claim 36, further comprising drying the sodium hyaluronate by nitrogen under sterile conditions.

* * * * *